United States Patent
Torcheboeuf

(10) Patent No.: US 6,843,182 B2
(45) Date of Patent: Jan. 18, 2005

(54) OPERATING TABLE, DESIGNED IN PARTICULAR FOR SURGICAL OPERATIONS

(75) Inventor: Bruno Torcheboeuf, Volgre (FR)

(73) Assignee: ALM, Ardon (FR)

( * ) Notice: Subject to any disclaimer, the term of this patent is extended or adjusted under 35 U.S.C. 154(b) by 0 days.

(21) Appl. No.: 10/343,309

(22) PCT Filed: Aug. 8, 2001

(86) PCT No.: PCT/FR01/02578

§ 371 (c)(1), (2), (4) Date: Oct. 10, 2003

(87) PCT Pub. No.: WO02/11618

PCT Pub. Date: Feb. 14, 2002

(65) Prior Publication Data

US 2004/0060482 A1 Apr. 1, 2004

(30) Foreign Application Priority Data

Aug. 8, 2000 (FR) .............................. 00 10434

(51) Int. Cl.⁷ .............................................. A47B 11/00
(52) U.S. Cl. ........................... 108/143; 5/600; 428/424
(58) Field of Search ...................... 108/143, 20; 5/600, 5/601, 81.145; 378/209; 248/657, 424, 429

(56) References Cited

U.S. PATENT DOCUMENTS

| 3,155,383 A | * | 11/1964 | Whitmore .................. 108/143 |
| 3,452,977 A | * | 7/1969 | Ryman ....................... 108/143 |
| 3,868,103 A | * | 2/1975 | Pageot et al. ............... 378/209 |
| 4,475,072 A | | 10/1984 | Schwehr et al. |
| 4,568,071 A | * | 2/1986 | Rice .............................. 5/601 |
| 5,410,767 A | * | 5/1995 | Barud ........................... 5/601 |
| 5,533,844 A | * | 7/1996 | Ekleberry ................... 108/143 |
| 6,459,923 B1 | * | 10/2002 | Plewes et al. .............. 378/209 |
| 6,615,428 B1 | * | 9/2003 | Pattee ........................ 108/143 |
| 6,615,429 B2 | * | 9/2003 | Weil et al. .................. 378/209 |

FOREIGN PATENT DOCUMENTS

| EP | 0 200 374 | 12/1986 |
| FR | 2.193.321 | 2/1974 |
| FR | 2 529 088 | 12/1983 |
| JP | 03233760 A | * 10/1991 ........... G06F/15/20 |

* cited by examiner

Primary Examiner—Jose V. Chen
(74) Attorney, Agent, or Firm—Young & Thompson

(57) ABSTRACT

A table comprising a base (2), a vertical pillar (4), a horizontal platform (5) provided with a seat (9) and mounted on the pillar, and elements for moving the platform relative to the pillar, the elements comprise, a first rail (12), secured to the pillar, a second rail (13) parallel to the lower rail, integral with the seat and mobile in translation therewith relative to the first rail, and a carriage (15) mounted freely sliding on the first fixed rail from one end thereof to the other, the second rail being mounted sliding relative to the carriage and thereon; on each rail (12, 13) a shoe is mounted sliding, said shoe being mechanically integral with the carriage (15).

7 Claims, 6 Drawing Sheets

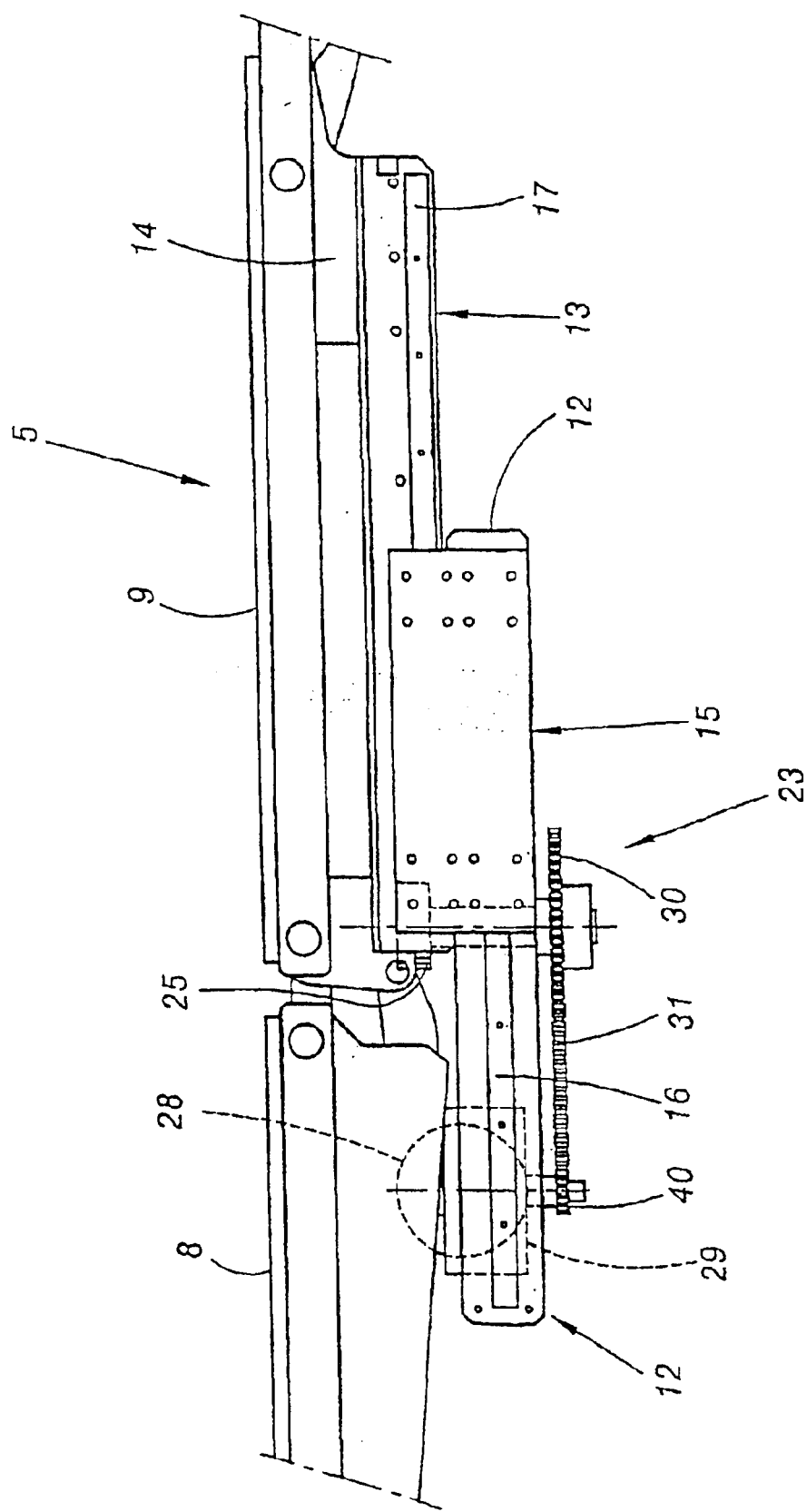

OPERATING TABLE, DESIGNED IN PARTICULAR FOR SURGICAL OPERATIONS

The present invention relates to an operating table, designed particularly but not exclusively for surgical operations, the table being of the type comprising a baseplate, a vertical pillar mounted on the baseplate, a horizontal platform provided with a seat and mounted on the pillar, and means for moving the platform in translation relative to the pillar on either side thereof.

In surgical applications, an operating table of this type is associated with radiological equipment which may be generally C-shaped, which is why it is commonly referred to as a "C-arm", carrying radiological means at its ends in order to be able to take X-rays of different parts of a patient's body. These X-rays are taken by moving the radiological system around the longitudinal axis of the table, or around an axis extending transversely thereto at one of its ends.

The radiological apparatus thus tilts either about the longitudinal axis of the table or else about an axis extending transversely thereto in order to enable the radiological device to be positioned appropriately. Such equipment is also used with radiology tables in which the platform supporting the patient is cantilevered out from its support pillar. Such a radiological table can be used only for minor surgical operations.

The platform of the operating table to which the invention relates more particularly comprises in conventional manner a headrest for receiving the patient's head, a section for receiving the back, a seat for receiving the patient's behind, and an end section for supporting the legs.

A drawback associated with that structure for an operating table comes from the support pillar which constitutes an impediment for taking certain X-rays, such that in practice only zones outside relative to the pillar enable satisfactory X-rays to be obtained. To overcome that difficulty, proposals have been made to turn the patient round, placing the patient's head where the feet were, and vice versa, while the patient is at this stage unconscious under anesthetic. In the usual operating procedure, a surgeon enters the operating theater only after the patient has been prepared and anesthetized, and it often happens that the surgeon finds that the patient has not been positioned properly.

If necessary, in a first embodiment of the known operating table, use is made of mechanical extension pieces with which the table is fitted. That requires handling to be performed that is awkward and involves the major drawback of turning the patient round which can endanger patient safety since turning an anesthetized patient round can give rise to accidents in handling.

In addition, during such handling, the structure of the table may become unbalanced relative to its center of gravity which can run the risk of the patient falling.

Proposals have therefore been made for a second embodiment of the operating table in which the platform is mounted to pivot about a vertical axis passing through the support pillar. Such a structure presents the advantage of avoiding the need to turn the anesthetized patient round, but it still runs the risk of the table toppling when it has pivoted through 90° since the platform is not symmetrical about the vertical axis of the support pillar. To avoid that risk it is necessary to draw the patient's legs up, and that too is undesirable when the patient is anesthetized. In addition, a table of that structure also requires extension pieces to be handled mechanically in various ways.

Another drawback of those known tables lies in the considerable height of the longitudinally-extending side members of the table support and in the insufficient width between them defining an X-ray window. This gives rise to considerable bulk, leading to difficulties and limitations on the access of X-ray equipment between the side members and beneath the seat, significantly reducing the options for taking X-rays.

A third embodiment has also been proposed in which the table includes a platform support that can be moved in translation relative to the support pillar by means of an actuator device. That type of table raises technical problems associated with constraints on dimensions. For mechanical reasons, the width of the support pillar cannot be less than about 500 millimeters (mm) in practice. Unfortunately, it is desirable for it to be possible to move the table in translation likewise through 500 mm, i.e. a stroke which is at least as great as the width of the support column or pillar. Furthermore, in order to limit the size of the guide system, the length of the control actuators cannot exceed the length of the "seat" section of the table, which in a surgical table is ideally about 400 mm. Finally, an actuator having a stroke of 500 mm needs to be at least 600 mm long because of a non-reducible "dead" length of the actuator.

It will thus be understood that that structure does not completely solve the problem posed which consists essentially in providing the platform with a stroke of length that is sufficient in spite of the width of the support pillar which, in practice, cannot be reduced to less than about 500 mm, while still making it possible to bring the X-ray device close enough under the table vertically in order to take satisfactory X-ray pictures in zones close to the pillar, i.e. where access is difficult.

The operating table in the last above-described embodiment enables simple translation to be performed through 500 mm by means of the control actuators, but the width of the X-ray window is insufficient (290 mm because of the bulk of the actuator system) while its height is excessive (about 190 mm) and consequently reduces the size of the X-ray picture obtained.

In general, the various known embodiments of operating tables are of large bulk, of "retracted" or "shortened" length considerably greater than the stroke of the platform, of height that is excessive, of width that is insufficient, and finally of load-bearing capacity that is limited. The load-bearing limitation can be very troublesome for heavy patients.

An object of the invention is to provide an operating table in which the guide structure for the platform is arranged in such a manner as to overcome those drawbacks.

In accordance with the invention, the means for moving the platform of the table in translation relative to the support pillar comprise, on either side of the seat of the platform, a bottom first substantially horizontal rail fixed to a top end of the pillar, a top second substantially horizontal rail placed above the bottom rail and parallel therewith, the top rail being secured to the seat and movable in translation therewith relative to the bottom first rail, and a carriage mounted to slide freely horizontally on the stationary bottom rail from one end to the other thereof, the top rail being mounted to slide horizontally relative to the carriage and on the carriage.

Such a device for guiding the platform in translation presents a structure that is somewhat telescopic, making it possible to obtain a working stroke for the platform that is equal to or even greater than its "retracted" length, i.e. in practice, the width of the support pillar.

The operating table of the invention provided with such a device for guiding the platform in translation presents the essential advantage of satisfying the following constraints:

a) the minimum "retracted" length of the guide device is contained within the length of the "seat" section of the platform, i.e. the width of the support column, while still providing a working stroke that is at least equal thereto;

b) the width of the guide device is as small as possible in order to be able to leave as wide as possible an X-ray transparent window between the two side bars of the seat; and c) the height of the guide device is small enough to make it easy to handle X-ray devices of the C-arm type, for example beneath the seat, in particular in the upside-down position.

According to a characteristic of the invention, a respective shoe is slidably mounted on each moving top and stationary bottom rail pair, rolling elements being interposed between the shoes and the corresponding rails, and said shoes being mechanically secured to the carriage.

By way of example, the rolling elements may be balls, components that are well understood, particularly in the field of machine tools, and that enable heavy loads to be taken up by means that are compact.

Each rail carries an outwardly-directed side bar for supporting and guiding the shoe and the rolling elements, the shoe being of U-shaped section, for example, and placed around the side bar and partially received in the carriage.

By way of non-limiting indication, the dimensions of the device for providing guidance in translation may be as follows for each side bar of the seat and for a stroke of 500 mm: "retracted" length 500 mm; width 60 mm; and height 100 mm; thus leaving an X-ray access window of very satisfactory dimensions beneath the platform. The load-bearing capacity of the table can exceed 300 kilograms (kg).

Other features and advantages of the invention appear from the following description made with reference to the accompanying drawings which show an embodiment by way of non-limiting example.

FIG. 5 is a longitudinal elevation view analogous to FIG. 4 showing the platform and the device for guiding it in translation in the opposite extreme position.

Figure 1:
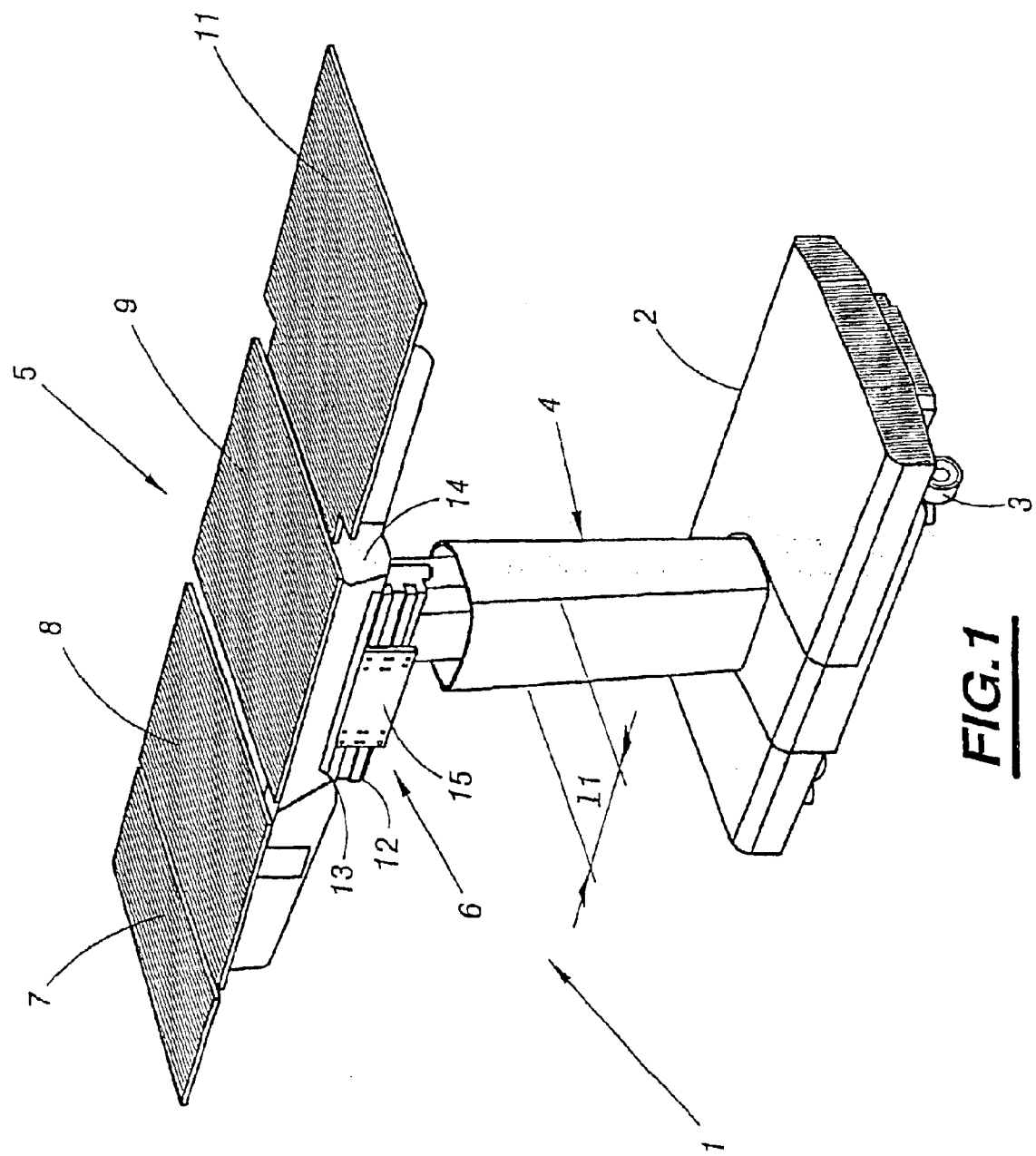
FIG. 1 is a small-scale perspective view of an embodiment of an operating table of the invention.
Figure 2:
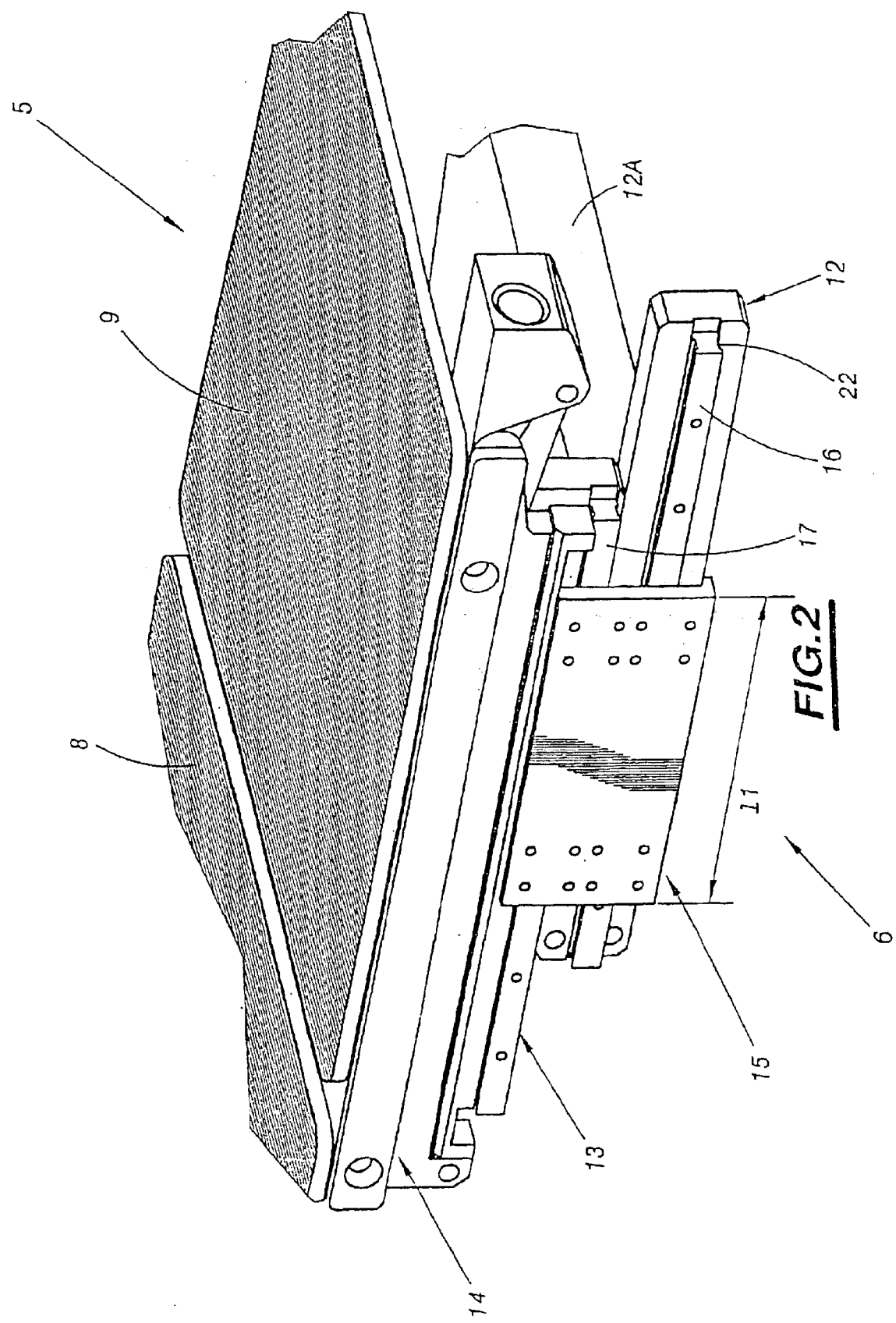
FIG. 2 is a fragmentary perspective view on a larger scale than FIG. 1 showing the device for guiding the seat section of the platform in translation, and thus for guiding the platform.

The operating table 1 shown in FIG. 1 comprises a baseplate 2 mounted on castors 3, a pillar or column 4 mounted vertically on the baseplate 2, a horizontal platform 5 mounted on the support pillar 4 and extending on either side thereof, and a guide device 6 for moving the platform 5 in translation relative to the pillar 4 on either side thereof.

The table 1 is particularly but not exclusively suitable for use as a surgical table, in which case the platform 5 is adapted to receive an anesthetized patient (not shown). For this purpose, the platform 5 has a headrest-forming section 7 for receiving a patient's head, a section 8 for serving as a support for the patient's back, a seat section 9 for receiving the patient's behind which is placed on top of the pillar 4, and finally an end section 11 that is designed to serve as a leg rest. Naturally, the dimensions of these various sections may vary depending on the corpulence of the patient.

There follows a more particular description with reference to FIGS. 2 to 5 of the means 6 for guiding the platform 5 in translation.

On either side of the seat 9 of the platform 5, these means comprise a bottom first substantially horizontal rail 12 fixed to a top end of the pillar 4 via suitable means that are conventional and not shown, for example two cross-members 12A.

The guide device 6 also comprises a top second substantially horizontal rail 13 placed above the bottom rail 12 and parallel thereto. The top rail 13 is secured to a side bar 14 of the seat 9 and is movable in translation therewith, and thus with the entire platform 5, relative to the stationary bottom first rail 12.

The device 6 for providing guidance in translation also comprises, for each of the two pairs of rails 12, 13 a carriage 15 that is mounted to slide freely horizontally on the stationary bottom rail 12 from one end thereof to the other. The moving top rail 13 is mounted on the carriage 15 and can slide horizontally relative thereto.

Each rail 12 and 13 carries on its outside a respective side bar 16, 17 extending longitudinally on the outside face of the corresponding rail. Each projecting side bar 16, 17 carries a respective sliding shoe 18, 19 of substantially U-shaped cross-section so as to cover or hide the corresponding supporting side bar 16, 17, and with rolling elements 21 being interposed between the side bar and the corresponding shoe 18, 19. By way of example, the elements 21 can be metal balls housed in grooves 22 of the side bars 16, 17, which thus co-operate with the balls 21 to constitute rolling bearings for the shoes 18, 19.

The shoes are mechanically secured to the carriage 15 in which they are partially received.

Figure 3:
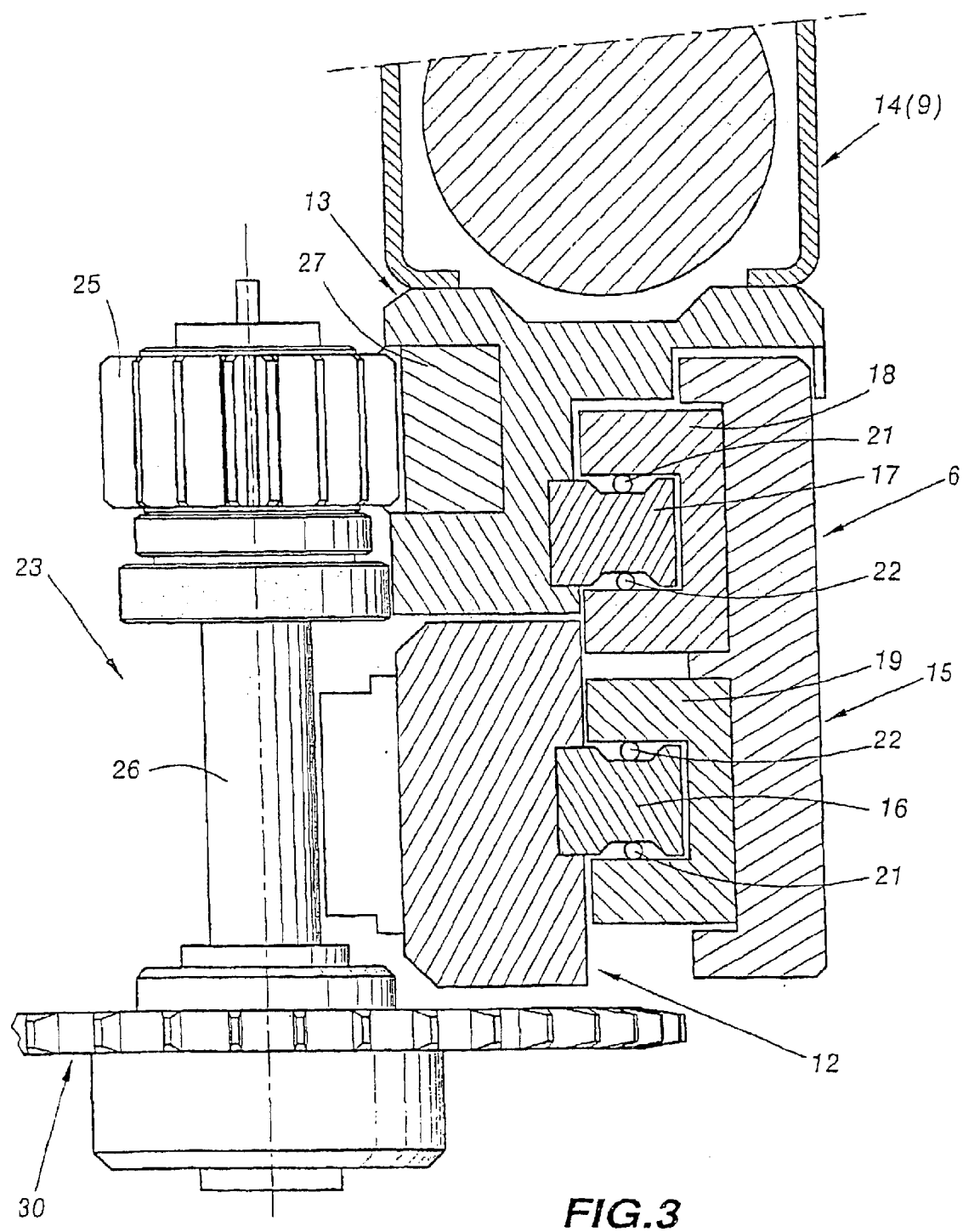
FIG. 3 is a view partially in cross-section and partially in elevation of the device for guiding the platform of the table of FIGS. 1 and 2 in translation.
Figure 4:
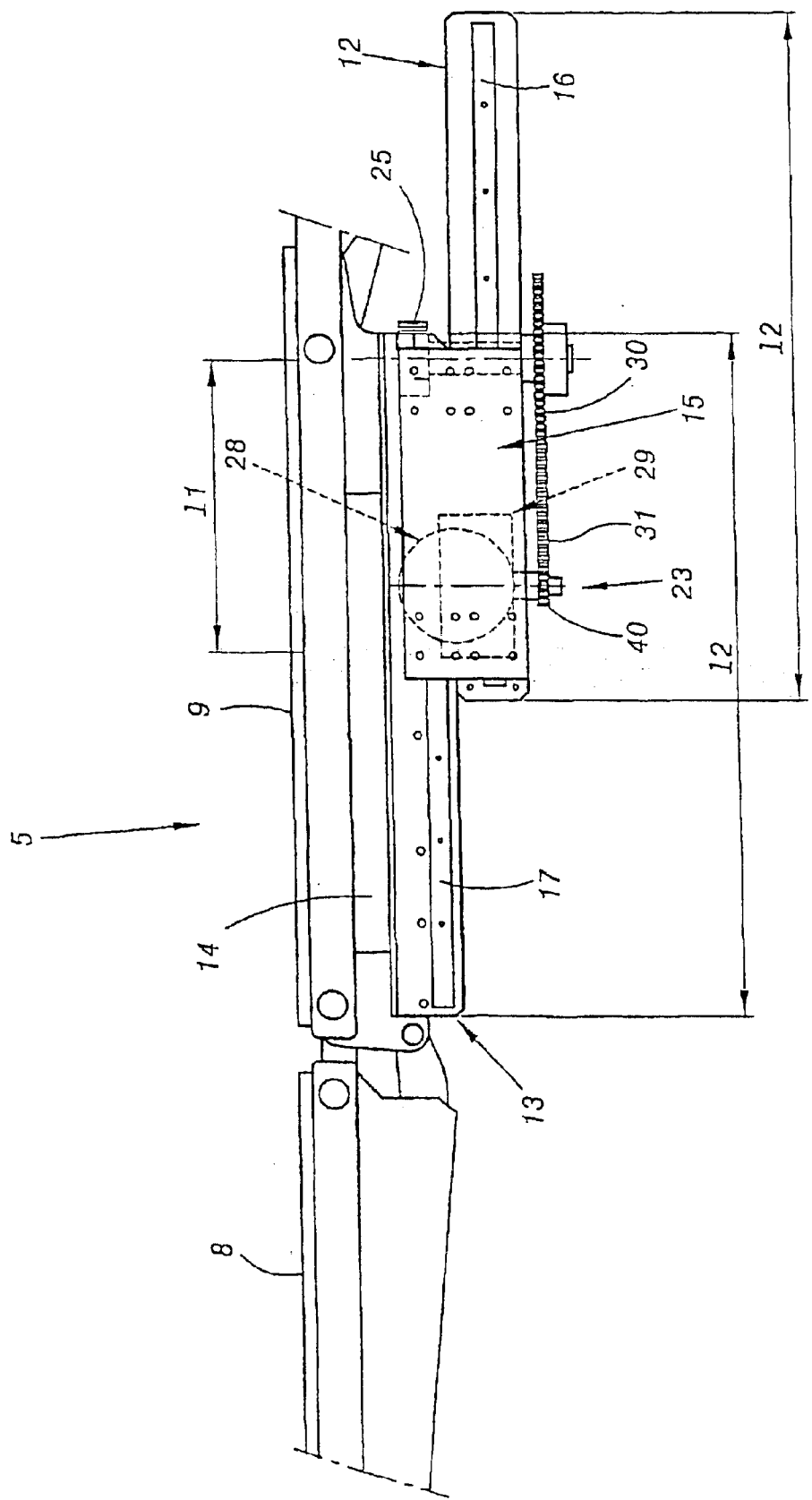
FIG. 4 is a longitudinal elevation view of the device for guiding the platform of the table in translation, the device being shown in one of its extreme positions.

The operating table 1 is additionally provided with means for driving in translation the top rail 13 of each of the two lateral devices 6 for guiding the seat 9 relative to the stationary bottom rail 12. These means, an embodiment 23 of which is shown in FIGS. 3 to 5, are mounted on a stationary support beneath the seat 9 and extend substantially vertically beside the rails 12 and 13.

In the embodiment shown, these drive means comprise, for each pair of rails 12 and 13, a motor and gear box unit 28, a stepdown gearing stage 29 associated with the outlet wheel from the motor unit and having an outlet pinion 40 driving a sprocket wheel 30 by means of a chain 31. The sprocket wheel 30 turns with a shaft 26 carrying an end pinion 25. Its function is to drive the moving top rail 13 in translation, e.g. by meshing with a longitudinal rack 27 received in the top rail 13 and secured thereto (FIG. 3).

Figure 6A:
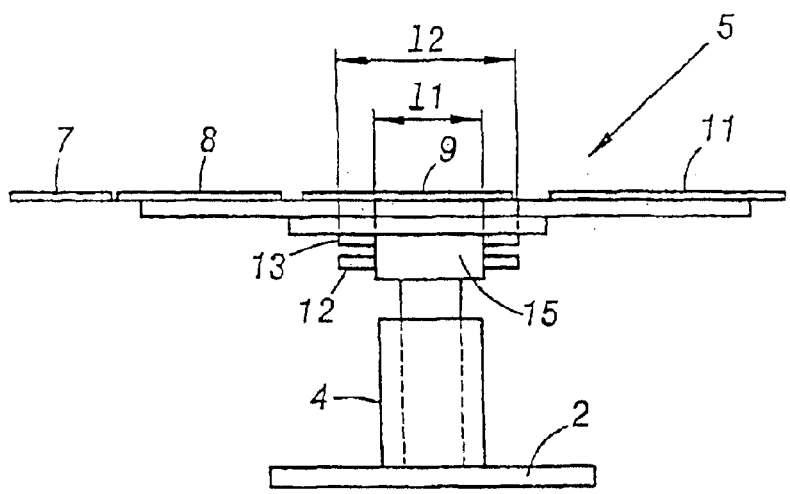
FIG. 6A is a simplified longitudinal elevation view of the operating table of FIGS. 1 to 5 in its middle position, its translation guidance mechanism being "retracted".

The carriage 15 is of a length l1 substantially equal to the width l1 of the pillar 4. The total stroke possible for the seat 9 and the platform 5 in translation by means of the two lateral guide devices 6 of the kind described above is shown in FIGS. 4 and 5. The two rails 12 and 13 are of a length l2, with the extreme position shown in FIG. 4 (corresponding to FIG. 6B) being obtained from the central position shown in FIG. 6A as follows. In the position shown in FIG. 6A, the moving top rail 13 lies exactly above the stationary bottom rail 12, vertically above it so that the ends of these rails are in register vertically. In addition, the carriage 15 is occupying the central zone of the rails 12 and 13, being exactly in register with the pillar 4.

Figure 6B:
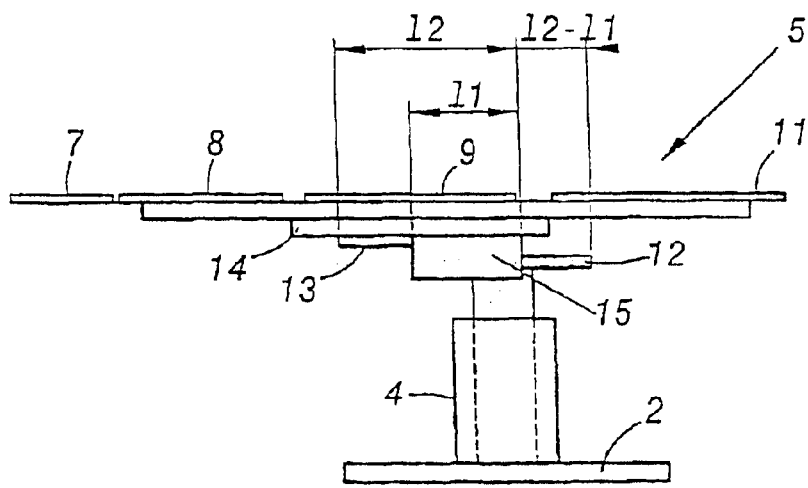
FIG. 6B is a simplified elevation view similar to FIG. 6A showing the table in its extreme position of FIG. 4.

The operator causes the carriage 15 to slide to the left, which carriage is free to move on the stationary rail 12. The movement of the carriage 15 entrains the entire platform 5 to the left until the carriage 15 comes into abutment against the left hand end of the rail 12. Then, by switching on the motor unit 28, the operator causes the top rail 13 to slide relative to the carriage 15 which has reached its abutment, thereby moving the platform 5 through a new stroke in translation relative to the carriage 15 and the stationary rail 12, until the extreme position is reached (FIGS. 4 and 6B).

Figure 6C:
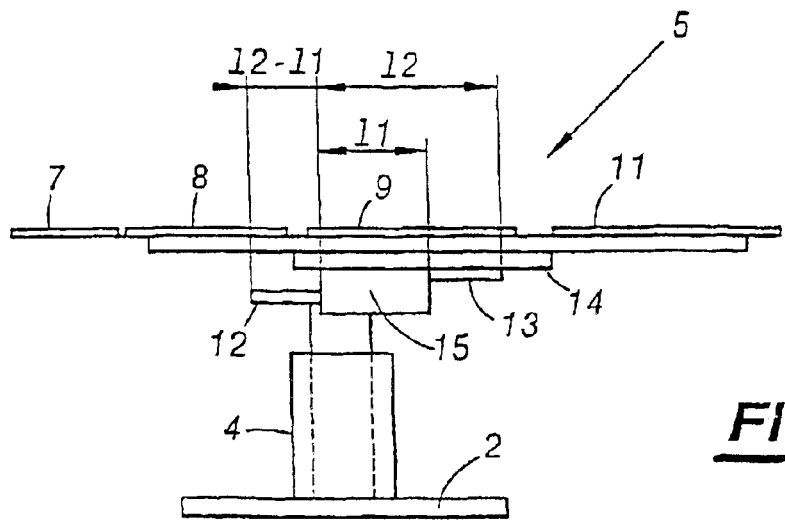
FIG. 6C is a simplified elevation view similar to FIGS. 6A and 6B showing the table in the extreme position of FIG. 5.

Starting from this extreme position, the platform 5 can be taken to its opposite extreme position (FIGS. 5 and 6C) by proceeding as follows: The operator causes the carriage 15 to slide from one end to the other of the bottom rail 12 until the carriage 15 comes into abutment thereagainst. During this movement, the platform 5 is moved in translation through a stroke equal to $l2-l1$.

Thereafter the operator starts the motor unit 28 which acts via the sprocket wheel 30 and the pinion 25 to drive the top rail 13 together with the platform 5 in translation relative to the carriage 15 through an additional stroke of $l2-l1$.

The total stroke between FIGS. 4 and 5 (6B and 6C) is thus:

$$2(l2-l1)$$

For this to be possible, it is necessary for $l1$ to be less than or equal to $l2/2$. In practice, for mechanical reasons, the best compromise is achieved for $$l1=l2/2$$

It is necessary for the carriage 15 to have a minimum length that is suitable, since otherwise it would be necessary to increase the height of the rails 12 and 13 which would impede good access for X-ray devices between the two pairs of rails 12 and 13.

Thus, the total stroke obtained for the table 5, ignoring the meshing width of the teeth of the pinion 25, is nearly equal to the length l1 of the carriage 15 and to the width of the pillar 4, e.g. 500 mm. Under such conditions, the height of the side members, i.e. the total height of the rails 12 and 13, can be reduced to about 160 mm, and the width of the X-ray window between the rails can be about 390 mm, which values are highly satisfactory, and enable very good quality X-rays to be obtained.

The invention is not limited to the embodiment described and may comprise a range of variants. By way of example, the drive system using an electric motor and a rack-and-pinion system may be replaced by any other equivalent apparatus. Similarly, possible applications for the same table are very general, and its use as surgical table being given purely by way of example.

What is claimed is:

1. An operating table for use in particular in surgical operations, the table comprising a baseplate, a vertical pillar mounted on the baseplate, a horizontal platform provided with a seat and mounted on the pillar, and means for moving the platform in translation relative to the pillar on either side thereof, wherein said means comprise, on either side of the seat of the platform, a bottom first substantially horizontal rail fixed to a top end of the pillar, a top second substantially horizontal rail placed above the bottom rail and parallel therewith, the top rail being secured to the seat and movable in translation therewith relative to the bottom first rail, and a carriage mounted to slide freely horizontally on the stationary bottom rail from one end to the other thereof, the top rail being mounted to slide horizontally relative to the carriage and on the carriage.

2. A table according to claim 1, wherein a shoe is slidably mounted on each moving top and stationary bottom rail, rolling elements being interposed between each shoe and the corresponding rail, and said shoes being mechanically secured to the carriage.

3. A table according to claim 2, wherein each rail carries an outwardly-directed side bar for supporting and guiding the shoe and the rolling elements, the shoe being of U-shaped section, for example, and placed around the side bar and partially received in the carriage.

4. A table according to claim 1, the table being provided with means for driving in translation the top rail and the seat of the platform relative to the stationary bottom rail, and wherein said means are mounted on a stationary support beneath the seat.

5. A table according to claim 4, wherein said drive means comprise an electrical motor and gear box unit, a demultiplication gear stage associated with an outlet wheel from the motor unit, said stage being provided with an end pinion for driving the movable top rail.

6. A table according to claim 5, wherein the end pinion meshes with a longitudinal rack received in the top rail and secured thereto.

7. A table according to claim 1, wherein the carriage is of a length l1 substantially equal to the width l1 of the pillar such that, for the two rails having the same length l2, the total stroke of the movable top rail is equal to substantially twice the length l2 of the bottom rail minus the length l1 of the carriage.

* * * * *